(12) United States Patent
Ramsey et al.

(10) Patent No.: US 10,166,076 B2
(45) Date of Patent: Jan. 1, 2019

(54) REGISTRATION OBJECT, CORRECTION METHOD AND APPARATUS FOR COMPUTED RADIOGRAPHIC TOMOGRAPHY

(71) Applicant: NIKON METROLOGY NV, Leuven (BE)

(72) Inventors: Andrew Timothy Ramsey, Oxford (GB); Andrew Robert Ray, Tring (GB)

(73) Assignee: NIKON METROLOGY NV, Leuven (BE)

( * ) Notice: Subject to any disclaimer, the term of this patent is extended or adjusted under 35 U.S.C. 154(b) by 609 days.

(21) Appl. No.: 14/775,245

(22) PCT Filed: Mar. 27, 2014

(86) PCT No.: PCT/EP2014/055827
§ 371 (c)(1),
(2) Date: Sep. 11, 2015

(87) PCT Pub. No.: WO2014/154627
PCT Pub. Date: Oct. 2, 2014

(65) Prior Publication Data
US 2016/0030133 A1 Feb. 4, 2016

(30) Foreign Application Priority Data

Mar. 27, 2013 (GB) .................................. 1305658.5
Feb. 6, 2014 (GB) .................................. 1402082.0

(51) Int. Cl.
*A61B 6/00* (2006.01)
*A61B 19/00* (2006.01)
(Continued)

(52) U.S. Cl.
CPC .............. *A61B 19/54* (2013.01); *A61B 6/032* (2013.01); *A61B 6/5258* (2013.01); *A61B 6/583* (2013.01);
(Continued)

(58) Field of Classification Search
CPC ..... A61B 6/032; A61B 6/5205; A61B 6/5258; A61B 6/58; A61B 6/581; A61B 6/582;
(Continued)

(56) References Cited

U.S. PATENT DOCUMENTS 4,782,502 A 11/1988 Schulz
6,148,058 A 11/2000 Dobbs
(Continued)

FOREIGN PATENT DOCUMENTS

DE 20009714 10/2001
DE 202005004500 7/2006
(Continued)

OTHER PUBLICATIONS

International Search Report and Written Opinion for Application No. PCT/EP2014/055827 dated Jun. 25, 2014, 13 pages.
(Continued)

*Primary Examiner* — Thomas R Artman
(74) *Attorney, Agent, or Firm* — Andrew M. Calderon; Roberts Mlotkowski Safran Cole & Calderon, P.C.

(57) ABSTRACT

Disclosed is a registration object for computed radiographic tomography. The object has a body portion defining a void for including at least part of a target object. The registration object comprises one or more relatively radiopaque or relatively radiolucent features. Said feature or features provide, in a suitable proportion of radiographic projections of the registration object with respect to angle about a predetermined axis, a pair of identifiable registration points which are spaced apart in a direction parallel to the predetermined (Continued)

axis by a first distance, and whose positions in that direction are each either a constant or a function only of the angle of the projection about the predetermined axis. Said feature or features define, in the suitable proportion of radiographic projections of the object with respect to angle about a predetermined axis, a pair of identifiable registration points which are spaced apart in a direction perpendicular to the predetermined axis by a second distance whose positions in that direction are each either a constant or a continuous function only of the angle of the projection about the predetermined axis. The suitable proportion can be substantially all or all radiographic projections. Also disclosed are a method, an apparatus, a storage medium and a signal for correcting computerized radiographic tomography data, optionally using such an object.

49 Claims, 11 Drawing Sheets

(51) Int. Cl.
*A61B 6/03* (2006.01)
*G01N 23/046* (2018.01)
*G21K 1/10* (2006.01)
*A61B 90/00* (2016.01)
*G06T 11/00* (2006.01)

(52) U.S. Cl.
CPC ........... *A61B 90/39* (2016.02); *G01N 23/046* (2013.01); *G21K 1/10* (2013.01); *A61B 2090/3966* (2016.02); *G06T 11/005* (2013.01)

(58) Field of Classification Search
CPC ....... A61B 6/583; G06T 11/005; G06T 7/337; G06T 2207/10081; G06T 2207/30204; G06T 2207/30208
See application file for complete search history.

(56) References Cited

U.S. PATENT DOCUMENTS

| | | | |
|---|---|---|---|
| 7,599,468 B2* | 10/2009 | Zuendorf | A61B 6/14 378/38 |
| 8,958,865 B2* | 2/2015 | Hsu | A61B 6/037 324/321 |
| 9,113,798 B2* | 8/2015 | O'Brien | A61B 6/032 |
| 2005/0117708 A1 | 6/2005 | Cho | |
| 2006/0184014 A1 | 8/2006 | Pfeiler | |
| 2008/0144913 A1 | 6/2008 | Yoshida | |
| 2008/0253506 A1* | 10/2008 | Zuendorf | A61B 6/14 378/18 |
| 2008/0285827 A1 | 11/2008 | Meyer et al. | |
| 2010/0284601 A1 | 11/2010 | Rubner et al. | |
| 2011/0135053 A1 | 6/2011 | Noordhoek et al. | |
| 2012/0027167 A1* | 2/2012 | O'Brien | A61B 6/032 378/20 |
| 2013/0091966 A1* | 4/2013 | Hsu | A61B 6/037 73/866.4 |
| 2015/0297149 A1* | 10/2015 | Park | A61B 6/14 345/419 |
| 2016/0030133 A1* | 2/2016 | Ramsey | A61B 6/032 378/163 |

FOREIGN PATENT DOCUMENTS

| | | |
|---|---|---|
| EP | 2722018 | 4/2014 |
| WO | WO-2008038283 | 4/2008 |
| WO | WO-2012023876 | 2/2012 |

OTHER PUBLICATIONS

N. K. Strobel, "Improving 3D image quality of x-ray C-arm imaging . . . for calibrating the projection geometry", Proceedings of SPIE, vol. 5030, Jan. 1, 2003, pp. 943-954.
Intellectual Property Office document, 4 pages, date of search Sep. 24, 2013

* cited by examiner

REGISTRATION OBJECT, CORRECTION METHOD AND APPARATUS FOR COMPUTED RADIOGRAPHIC TOMOGRAPHY

FIELD OF THE INVENTION

The present invention relates to computed radiographic tomography, particularly computed radiographic tomography (CT) carried out using X-rays, and particularly to a registration object and method and apparatus for correcting data for use in that art.

BACKGROUND ART

Computed radiographic tomography is a well-known method for analysing the internal structure of various objects, parts of objects and target objects. It has use in diverse fields, including medical imaging, product quality control, and component defect analysis.

The basic concept of computerised radiographic tomography is shown in FIG. 1. FIG. 1 shows a source of radiation S and a detector D for the same type of radiation. The source S emits a beam B of the radiation which is detected at detector D. Interposed between source S and detector D is a target object T, the internal structure of which is intended to be analysed. As beam B of radiation passes through target object T, it is impeded to a greater or lesser extent depending on the properties and interaction path length of the material of target object T which is intersected by beam B. Detector D registers the intensity of radiation arriving from source S via target object T, usually as a two-dimensional pixel image. The image acquired this way is a projection of the target object T in terms of its transparency to the radiation. Such an image represents a projective view of the object from a single direction, and is essentially equivalent to a conventional radiographic image. X-ray radiation is the conventional choice of radiation, but other forms of radiation whose intensity is attenuated to different degrees by different internal structures or compositions of matter may also be selected, without limitation.

In computed radiographic tomography, the target object T is relatively rotated around axis A with respect to a reference frame defined by source S, detector D, and beam B. At small angular intervals of rotation, typically one tenth or one hundredth of a degree, a sequence of radiographic projections is acquired by detector D. After a complete circular rotation about axis A, the sequence of images so obtained, for example 3,000 to 30,000 images, typically up to 10,000, are synthesized into a volume map of object T in terms of the relative opacity of target object T to the selected radiation. While it is conventional to use a complete 360 degree rotation to obtain the sequence of images, in some cases it is acceptable to acquire images covering a rotation angle of at least 180 degrees.

Such a volume map can be used to determine the internal structure of target object T. The mathematical techniques used to transform the series of individual radiographic images, or radiographic projections as they are conventionally termed, into the volume map form part of the common general knowledge of one skilled in the art in this field, and are normally computerised or computer-implemented.

Depending on the type, and especially on the size, of target object T, the fixed reference frame for the rotation about axis A can be selected. In some cases, the source and detector can in opposition rotate about the axis A, for example in medical imaging applications where it is impractical to rotate a human body or body part as a whole. In other cases, when target object T is small, the object may be placed on a turntable and can be rotated about axis A while using a fixed source S and fixed detector D. This latter scenario is usual in industrial CT imaging.

However, as in all mechanical systems, misalignments, tolerances, and mechanical inaccuracies can cause deviations from the ideal system shown in FIG. 1. For example, the source and detector might relatively move during exposure, the relative rotation of the target object and source may not be perfect about axis A, and vibration and other effects can generally contribute to a less than optimal imaging or reconstruction situation. Especially, the axis of rotation can wobble or precess, or the source can expand due to heating during the exposure. Reconstructing volume maps from such imperfect imaging scenarios will generally result in a loss of detail and/or blurring in the acquired volume map.

Such errors in the relative movement of source and target object are a principal impediment to the development of high-resolution computerised radiographic tomography techniques, such as may be used for the analysis, for example, of very small electronic components or for very precise analysis of the human body. Improving useful resolution of the reconstructed volume map is an important goal in this field. However, it is very challenging to improve the accuracy of the mechanisms which create the relative movement necessary for computerised radiographic tomography. Therefore, the present inventor has recognised the need for a technique to minimise the effect such undesired movement has on the reconstructed volume map, rather than concentrating on improving the mechanical limitations of the imaging apparatus.

SUMMARY

According to the present invention, there is provided a registration object for computed radiographic tomography, the object having a body portion defining a void for including at least part of a target object, and the registration object comprising one or more relatively radiopaque or relatively radiolucent features, said feature or features providing, in a suitable proportion of radiographic projections of the registration object with respect to angle about a predetermined axis, a pair of identifiable registration points which are spaced apart in a direction parallel to the predetermined axis by a first distance, and whose positions in that direction are each either a constant or a function only of the angle of the projection about the predetermined axis and said feature or features defining, in the suitable proportion of radiographic projections of the object with respect to angle about a predetermined axis, a pair of identifiable registration points which are spaced apart in a direction perpendicular to the predetermined axis by a second distance whose positions in that direction are each either a constant or a continuous function only of the angle of the projection about the predetermined axis. The suitable proportion can be substantially all or all radiographic projections.

By providing such a registration object, when a volume map is acquired of a target object (a whole object, a part of a whole object, or a sample) included within the registration object, the registration points are identifiable in a suitable proportion of the radiographic projections and can be compared with known information about the registration object, and particularly with known information about the positioning of the features giving rise to the registration points, in order to extract, from each radiographic projection in which the registration points are identifiable, correction data which can be used to compensate for undesired relative movement of the source, target object and detector in each radiographic projection. Particularly, errors relating to along-axis and cross-axis shifts can be identified and eliminated, and changes in angle and magnification can be corrected. In addition, with precise dimensional information of the registration object, a correct scale can be assigned to the volume map.

According to a second aspect of the present invention, there is provided a method of correcting computerised radiographic tomography data, comprising the processes of: acquiring data representing a set of radiographic projections of a target object and a registration object including at least part of the target object within a void of the registration object at a series of angles about the predetermined axis; determining in each projection the positions of registration points defined by the registration object spaced apart in a direction perpendicular to the predetermined axis; comparing stored information about the registration object with the determined positions of the registration points to obtain projection correction information for each projection; applying the projection correction information to each projection to provide a set of corrected radiographic projections.

By providing such a method, errors due to relative movement of source and target object can be eliminated and therefore higher resolution volume maps can be created. Further, additional information about the target object, including actual dimensions of features, can be obtained.

According to a third aspect of the present invention, there is provided an apparatus for correcting computed radiographic tomography data, comprising a data acquisition module for acquiring data representing a set of radiographic projections of a target object and a registration object including at least part of the target object within the void of the registration object at a series of angles about the predetermined axis; a feature extraction module for determining in each projection the positions of registration points; a prediction module for predicting positions of the registration points in each projection; an error calculation module for comparing stored information about the registration object with the determined positions of the registration points to obtain error information for each projection; a transformation calculation module for determining transformations based on the error information; and a projection transformation module for applying the transformation to each projection to provide a set of corrected radiographic projections.

According to a fourth aspect of the present invention, there is provided a storage medium storing computer program instructions to program a programmable processing apparatus to become operable to perform the method according to the second aspect of the invention.

According to a fifth aspect of the present invention, there is provided a signal carrying computer program instructions to program a programmable processing apparatus to become operable to perform the method according to the second aspect of the invention.

BRIEF DESCRIPTION OF THE DRAWINGS

To better explain the present invention, and to show how the same may be carried into effect, reference will now be made, by way of example only, to the accompanying drawings, in which.

DESCRIPTION

Exemplary embodiments of the present invention will now be described.

Figure 2:
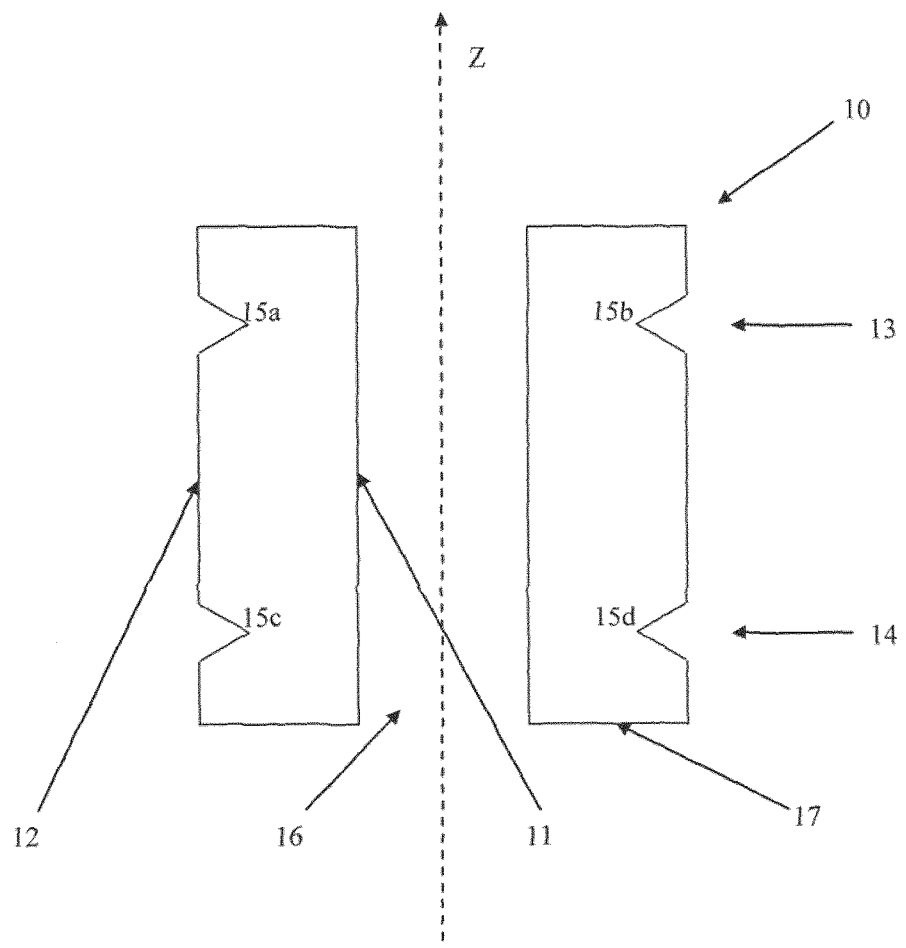
FIG. 2 shows an embodiment of a registration object for CT imaging, in cross-section.

A first embodiment of the present invention is shown in FIG. 2. FIG. 2 shows a vertical section through registration object 10, in a plane including axis Z. Registration object 10 has cylindrical symmetry about axis Z and is formed as a homogeneous cylindrical sleeve having a cylindrical void 16 defined by inner surface 11. The size of void 16 may be freely chosen so as to accommodate a desired target object, or part of a desired target object, to be imaged, hereinafter considered to be the target object under investigation. Outer surface 12 of object 10, which is coaxial with inner surface 11 of object 10 and with symmetry axis Z, has formed in it two annular grooves 13 and 14, each groove being formed in the circumferential direction around cylindrical surface 12 and being spaced apart in the Z-direction by a predetermined distance. In this embodiment, each groove has an identical profile, specifically, having a V-shape, with the apex of the V radially inward with respect to axis Z. The grooves of the embodiment shown in FIG. 2 extend radially about 25% of the wall thickness of the cylindrical sleeve and are separated by a distance along the Z-axis of around 80% of the total length in the Z-direction of registration object 10. The positions of groove 13 and groove 14 are essentially symmetrical about a plane bisecting registration object 10 in directions perpendicular to the Z-axis. The grooves are therefore displaced from each Z-axis end of registration object 10 by about 10% of the total length of the object.

Figure 3:
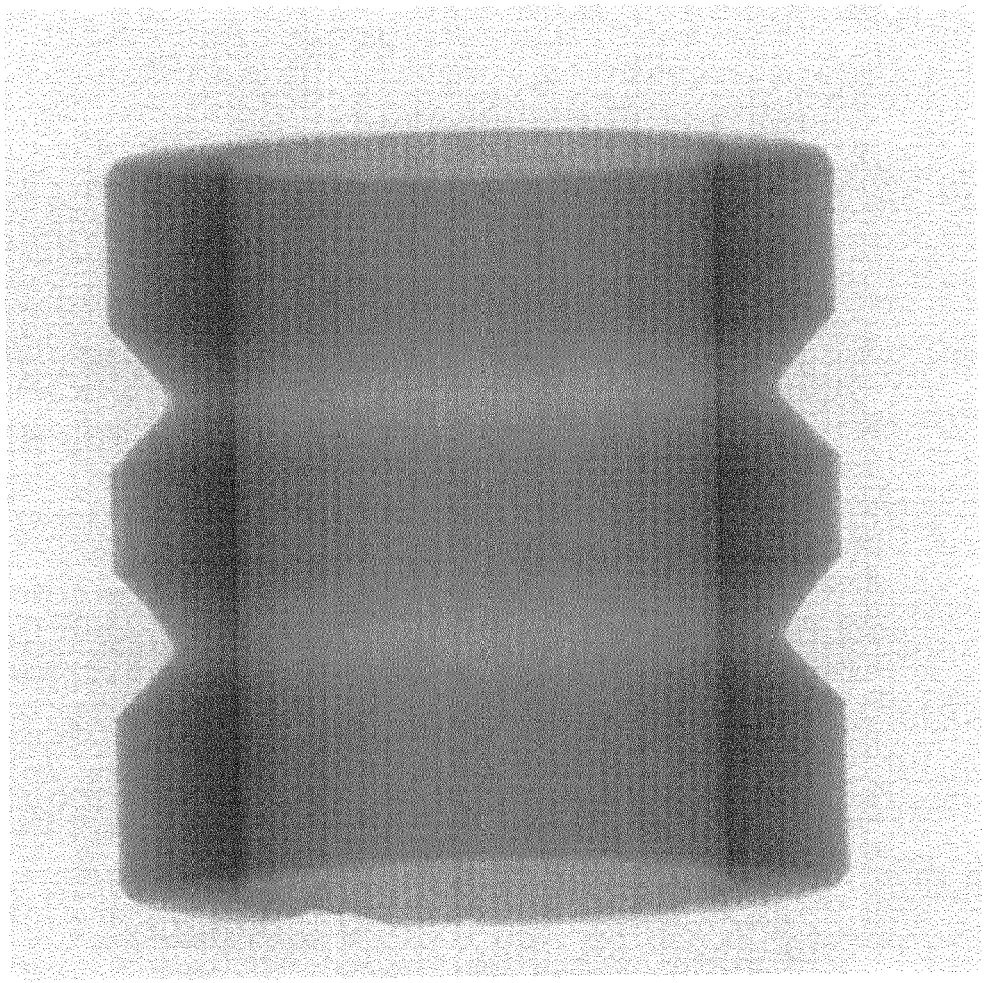
FIG. 3 shows the registration object of FIG. 2 in radiographic projection.

An X-ray projection in a direction perpendicular to the Z-axis through registration object 10 will produce a radiographic projection image similar to the view seen in FIG. 2, here shown as FIG. 3. The body of registration object 10 is relatively radiopaque, and is visible as a shadow area in the radiographic projection. Meanwhile, the grooves 13 and 14 are relatively radiolucent as compared with the body, and are therefore visible as contrasting (lighter-coloured) regions in the radiographic projection. The inwardly-facing tips of the V-shaped grooves are easily identifiable in the projection and define registration points 15a, 15b, 15c and 15d, whose positions may be used, together with known data about the actual or relative spacing of these points one from the other, to correct images of a target object placed in void 16 and imaged together with registration object 10.

This correction can be understood as follows. Since the relationship between the positions of registration points 15*a*, 15*b*, 15*c* and 15*d* are known for all projections of object 10 in directions perpendicular to the Z-axis, they provide a constant reference frame for the image of the target object enclosed in void 16. In particular, since registration object 10 has cylindrical symmetry, in a series of ideal radiographic projections taken from a series of angles about and perpendicular to axis Z, assuming perfect relative motion of source about registration object, the positions of registration points 15*a*, 15*b*, 15*c* and 15*d* are fixed in the projection.

Further, even when care is not taken to align an axis of cylindrical symmetry of the registration object with the axis of relative rotation of the source and detector, in a series of ideal radiographic projections about an axis parallel with but not coincident to axis Z, and perpendicular to axis Z, assuming perfect relative motion of source and registration object, the positions of registration points 15*a*, 15*b*, 15*c* and 15*d* undergo only regular sinusoidal motion in the Z-axis direction (as the object moves towards and away from the detector, equivalent to a magnification change) and in the cross-Z-axis direction (as the object moves side to side across the beam), with amplitude proportional to the offset between the axis about which the source-detector system and target object relatively rotates and with period equal to the period of the rotation. In some geometries, the sinusoidal motion in the Z-axis direction is negligible compared to the sinusoidal variation in the cross-Z-axis direction, and the positions of the registration points in the Z-axis direction can be treated as constant.

Therefore, in a realistic image acquisition, where undesired relative motion of source and target object exists and where the registration object is positioned to have a cylindrical axis substantially coincident with the axis of rotation of the source and detector, registration points 15*a*, 15*b*, 15*c* and 15*d* can be used to define a concrete reference frame for each radiographic projection. By transforming each radiographic projection acquired during a radiographic tomography sequence such that points 15*a*, 15*b*, 15*c* and 15*d* are always coincident, that is, at the same horizontal and vertical pixel positions, for each radiographic projection, unwanted relative motion of source and target object can be corrected.

Alternatively, even when the registration object is positioned to have a cylindrical axis being not substantially coincident with the axis of rotation of the source and detector the positions of the registration points can be recorded and fitted to a sinusoid in either the cross-axis direction alone or in both cross-axis and axial directions; deviations of the registration points from the expected sinusoid can be used to correct the unwanted relative motion. This latter approach applies the needed correction while maintaining the central axis of the reconstructed density map as the axis about which the source or target object rotates in the acquisition of the series of projections.

The registration object of FIG. 2 is particularly advantageous in having a base surface 17 perpendicular to axis Z on which the registration object is able to rest stably. This enables ease of use of the registration object, since, once a target object is placed on, for example, a turntable for radiographic imaging, the registration object can simply be placed to surround the object, and then can easily be removed after imaging is completed.

However, for different types of target object, alternative configurations of registration object are possible. For example, registration object 10 could be provided with a mount point internal to void 16 for mounting a target object at a defined location within the registration object, or indeed registration object 10 could be adapted for temporary fixation to the surface of a larger target object, such as a pipe or a body part. Such a configuration may be of special use in medical imaging, to correct errors caused by inadvertent movement of the body part between the acquisition of subsequent projections.

In general, when the registration object defines a void and encloses a target object within the void, the features of the registration object may be subject to essentially similar distortions and displacements, and thus may form a useful basis for correction of such distortions and displacements.

The arrangement of FIG. 2 is only one example of a large number of variations which are possible, as will be apparent to one skilled in the art from the present disclosure. An exemplary set of these are described below.

In the arrangement of FIG. 2, the grooves 13 and 14 are arranged to lie on and extend circumferentially about a surface of rotation around the Z-axis, namely an imaginary cylindrical surface coaxial with the outer surface 12 of registration object 10. However, a conical object could also be envisaged, wherein the two grooves are provided at different axial positions on a conical sleeve. Alternatively, other surfaces of rotation are possible, without limitation.

Furthermore, the position of the registration points 15*a*, 15*b*, 15*c* and 15*d* is constant in a projection perpendicular to the Z-axis for the registration object 10 of FIG. 2. However, this is not strictly necessary for the performance of the invention. In particular, provided that it is possible to determine from a complete sequence of radiographic projections about the axis Z (complete, in this sense, meaning a sequence of radiographic projections sufficient to perform a CT reconstruction, for example a sequence which substantially covers at least 180 degrees, preferably 360 degrees, about the axis), the expected relative positions of the registration points, a computer model of how the positions of the registration points varies with angle about the Z-axis at which the radiographic projection is acquired can be used to correct the acquired projection data. Hence, the expected relative positions of the registration points should be a continuous function of the angle of the projection about the Z-axis.

In this, it is preferred that the position of the registration points is an invertible function of the angle of the projection about the predetermined axis. By this, once a complete set of radiographic projections is acquired, the real spacing of the registration points represented by their image in the radiographic projection can be easily determined. In particular, it is preferred that the positions of the registration points are either constant or a linear function of the angle of the projection about the predetermined axis. More preferably, the object may be constructed such that the feature giving rise to the registration points has cylindrical symmetry. Such an object is easy to manufacture, and is also easy to analyse. However, in the most general case, all that is necessary is that the positions of the registration points are determined for each radiographic projection perpendicular to the Z-axis, and identifiable as registration points in the radiographic image.

The object of FIG. 2 exhibits V-shaped grooves as the features which define the registration points. V-shaped grooves are preferred, since they are easy to manufacture by machining and provide a precise and easily identifiable registration point at the tip of the V-shaped groove in a radiographic projection, especially for automated or computerised image processing. However, other means of defining the registration points are possible. For example, the grooves need not be V-shaped, but could have another cross-section, such as a semi-circular cross-section or a square cross-section. However, such cross-sections require more complex image analysis to determine repeatably a well-defined point within in the groove, and are consequently considered less advantageous in circumstances where precision is paramount. However, in some situations, they may be easier to manufacture and thus might be selected by one skilled in the art.

Figure 4:
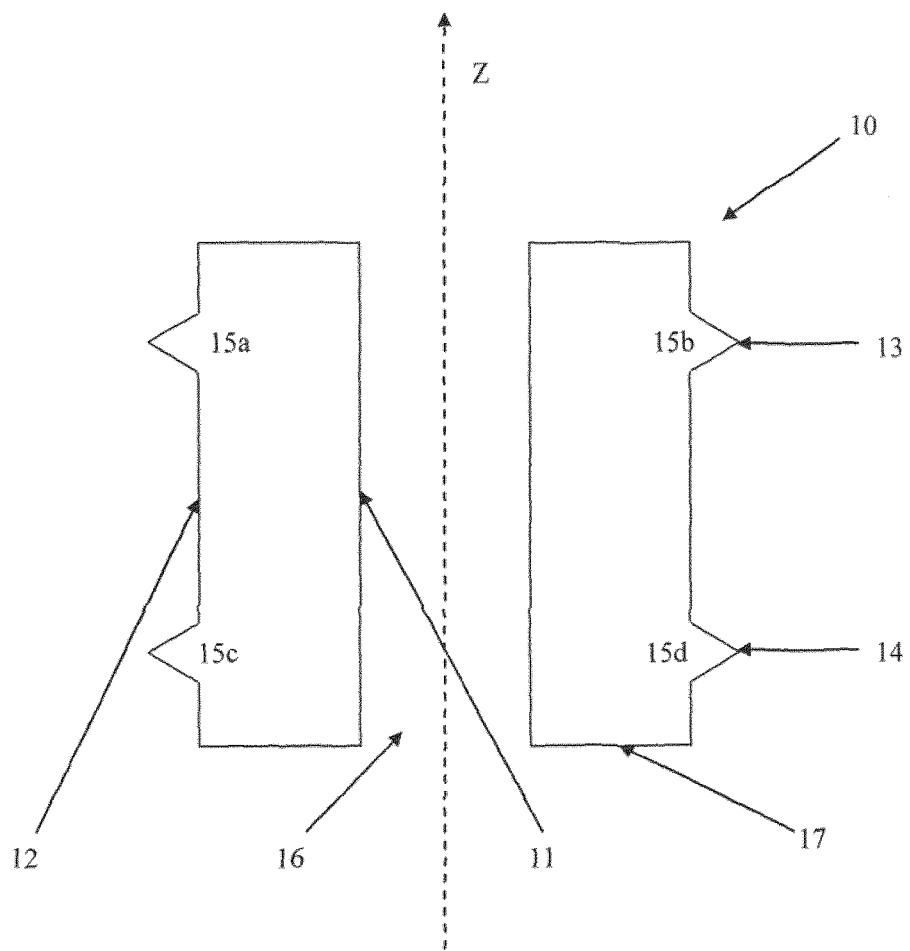
FIG. 4 shows another embodiment of a registration object for CT imaging, in cross-section.
Figure 5:
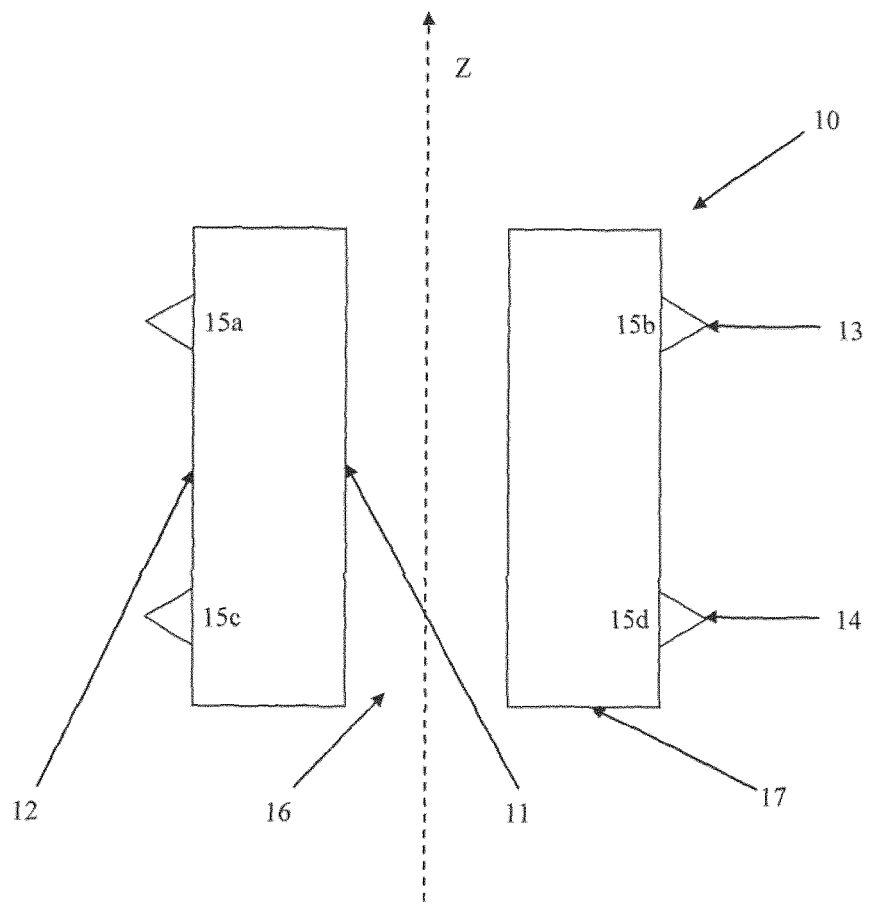
FIG. 5 shows a further embodiment of a registration object for CT imaging, in cross-section.

Alternatively, rather than a groove, a relatively radiopaque bead can be provided. This can, for example, as shown in FIG. 4, comprise an annular projection of the same material from which the body of the registration object is formed, or can comprise a relatively more radiopaque material fixed to the surface of the body of the registration object. Such is shown in, for example, FIG. 5. However, a relative disadvantage of this arrangement relative to embodiments employing grooves is that the bead may, with certain target objects, obscure critical features of the target object.

Figure 6:
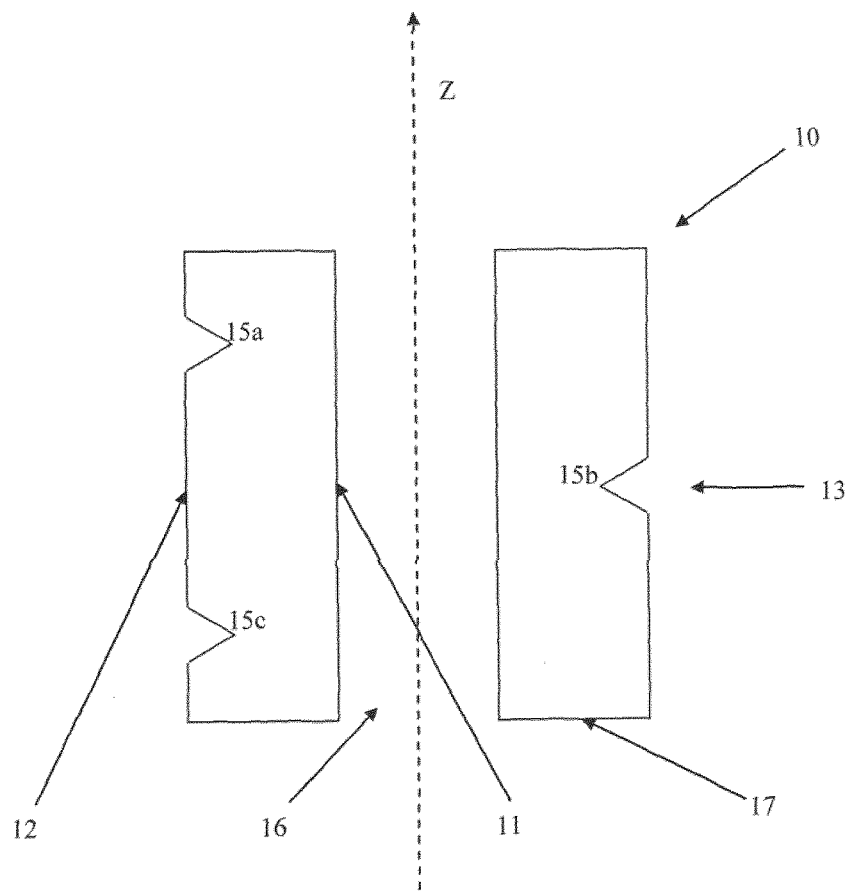
FIG. 6 shows a yet further embodiment of a registration object for CT imaging, in cross-section.

In FIG. 2, the features giving rise to the registration points are annular circumferential grooves 13 and 14 on the outer surface. However, alternative features are contemplated. For example, a single helical groove, or helical bead, could define the registration points, as shown in FIG. 6. While FIG. 6 shows three registration points, being the special case where the start and end of the helical feature is imaged, such an arrangement provides at least two registration points in each projection. Nevertheless, two points are adequate for providing image correction data, since the two points are separated in a direction parallel to the Z-axis, and are also separated in a direction perpendicular to the Z-axis.

In other embodiments, the groove or bead could instead be provided on the inner surface rather than the outer surface, or on both the inner surface and the outer surface. By positioning the groove or bead at a radially outer surface of the object, the contrast obtainable for the shape of the grooves in cross-section may be high, and thus the registration points may easily be identified in each projection. Positioning the groove or bead at a radially inner surface, such as that defining the void, may also be acceptable, although occlusion with portions of the object in front and behind a slice crossing the axis of the object may require more discriminating image processing to allow accurate identification.

In the embodiment of FIG. 2, void 16 extends to both axial ends of the body of registration object 10. This enables easy placement of the registration object around a target object. However, even for placement of the registration object around a target object on a surface, an opening at a single end of the registration object is adequate. The opening can be at the same end of the object as base surface 17, so that the registration object can be placed over a pre-positioned target object, or the void can open at the other axial end of the object, or at another location on the surface of the object, so that the registration object may be placed in position and then the target object can be placed in the registration object. A further possibility is that the body portion has first and second partial portions which are releasably engageable to enclose a target object, for example in a clam-shell manner. In such an arrangement, the void need not extend to any surface of the object.

In the arrangement of FIG. 2, the void is defined by a cylindrical inner surface 11 of the registration object 10 which is coaxial with the outer cylindrical surface 12 of the registration object 10. This arrangement is preferable, in that the projection of the material of the registration object between inner surface 11 and outer surface 12, in other words, the thickness of the cylindrical sleeve, provides a further measurable reference dimension for the image correction process. For example, the distance between lines defined to lie halfway between the projection of the inner surface and the projection of the outer surface on each side of the object, respectively, is one exemplary reference dimension. However, such an arrangement is not essential for the working of the invention.

Particularly, the void may be defined by a conical inner surface of the registration object, by a surface of rotation about the Z-axis which is neither conical nor cylindrical, or may be some other form, such as being specifically shaped to accept a particular type of target object. For example, a rectangular void could accept a target object cuvette, while a custom registration object could also be produced with a void shaped to fit closely about the outer surface of a particular target object part with which it is intended to be used, such as an electronic component or precision mechanical part. However, presently preferred as the registration object is a cylindrical sleeve with a coaxial cylindrical bore, in terms of ease of manufacture and versatility in use.

Notably, the registration object may be preferably made of a homogenous material having a moderate radiopacity, such that the imaging of a target object placed within is not excessively obscured, but also sufficiently radiopaque that the registration points may be identified. Of course, in an embodiment having a radiopaque bead, rather than radiolucent grooves, it is preferred that the registration object, apart from the bead, has low radiopacity, and may in some cases be formed of a strong yet radiolucent mesh structure to which the bead is affixed. Alternatively, a scaffold structure, for example formed by a number of thin yet strong parallel rods arranged on a pitch circle about axis Z, about which the radiopaque bead or beads are wrapped, may be considered. In such structures, there will usually be a trade off between minimising the density of the structure and maximising its structural stability. Nevertheless, such variants remain within the scope of the present invention, and may be preferred in some applications.

A further variant is a combination of the embodiment having radiolucent grooves and the embodiment having a radiopaque bead. In some cases, the registration object may be provided with grooves, which are subsequently filled with either relatively radiolucent or radiopaque material. Such arrangements may be preferred in terms of ensuring that the registration points are easily visible in the radiographic projection.

Even in the case in which the grooves or beads are interrupted, for example by manufacturing imperfections or the like, since a projection, rather than a cross-section, is obtained as each image, the registration feature may still be visible in each projection as a result of the presence of the feature in cross-sections forward and behind the interrupted portion.

Even if the registration feature is obscured, indistinct or non-identifiable in a relatively small proportion of projections, since radiographic projections may be acquired at equally-spaced angular intervals of as little as 0.1 or 0.05 degree, it may suffice that the feature is visible in a set of projections taken at equally-spaced 5 degree intervals, 2 degree intervals, 1 degree intervals, 0.5 degree intervals, 0.2 degree intervals, 0.1 degree intervals, or 0.05 degree intervals about an imaging axis. As described below with regard to the method of FIG. 9, even when a relatively small proportion of projections do not clearly exhibit a feature, interpolation can be used to estimate the position of the corresponding reference point.

The above arrangements have been described with regard to general radiographic imaging. Preferably, the registration object is for use with X-ray imaging, although other radiographic imaging techniques are also contemplated. When X-ray imaging is contemplated, a suitable material for the body of the registration object is aluminium, which can be formed to have a sufficiently small thickness of material between the outer surface and the void so as not to impair the imaging of a target object placed therein while retaining reasonable structural stability.

Figure 1:
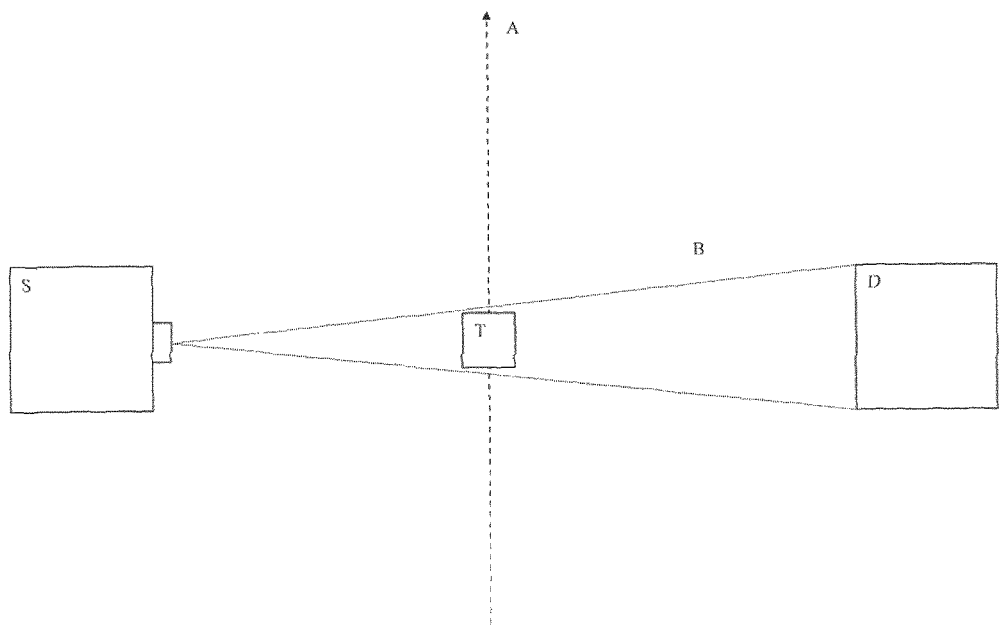
FIG. 1 shows a typical CT imaging scenario, in cross-section.

To produce a set of computerised radiographic tomography data using the registration object of FIG. 2, the geometry of FIG. 1 is adopted, with the registration object of FIG. 2 placed such that the axis Z is coincident with, or at least parallel to, the axis A and such that target object T lies within void 16. A set of radiographic projections of the target object is then acquired at a series of angles about axis A.

However, it is almost inevitable that in relative movement of the source S and the target object T about axis A, errors in the relative positioning of the source and the target object will occur. These may take the form of the source expanding or relatively moving towards or away from the target object (magnification errors), the source S moving in the direction of axis A relative to the target object T (axial movement errors) or the source S relatively moving perpendicular to axis A relative to target object T (cross-axis movement errors). Similar errors may occur with the position of the detector D relative to the source S or to the target object T. These errors may be corrected as follows.

Figure 7:
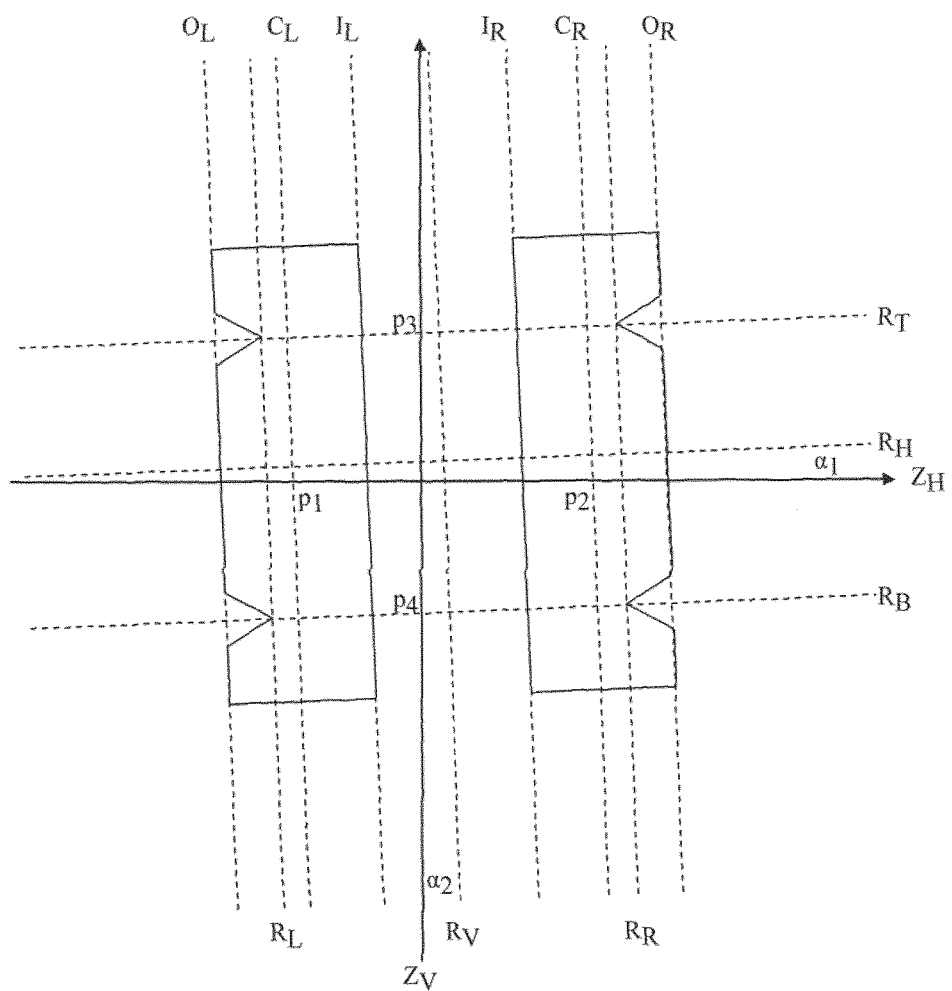
FIG. 7 shows a schematic projection of the registration object for CT imaging of FIG. 2, with reference lines used in error correction indicated.

As visible in FIG. 7, when a projection is obtained of the object of FIG. 2, a number of features of the registration object such as edges, grooves and projections may be identified by image-processing techniques such as feature extraction, edge detection and shape-matching. Any or all of these features, or their equivalents, may be used as reference points for correcting projections of a target object, thereby to improve the quality of the volume density map reconstructed from those projections. Similarly, where lines are identified, these lines can be used as reference points in one direction, or their intersections with each other or with predetermined reference lines can be equivalently used as reference points.

For example, in each projection of the target object T, the registration object 10 will also be visible in projection. Particularly, the registration points 15a, 15b, 15c and 15d will be visible in projection, together with the projected image of the target object.

Also, the relative axial distance between each of registration points 15a and 15b with respect to registration points 15c and 15d allows correction of the magnification of the image in the axial Z direction, while the relative distance between registration points 15a and 15c with respect to registration points 15b and 15d allows correction of the magnification in the cross-axis direction, for example as described further below.

Also, the mid-point between the line joining registration points 15a and 15b and the line joining registration points 15c and 15d defines an axial mid-point of the registration object and can be used to correct relative movement errors in the axial direction. Similarly, the mid-point of a line joining registration points 15a and 15c and the mid-point of a line joining registration points 15b and 15d defines a cross-axis mid-point of the registration object and can be used to correct relative movement errors in the cross-axis direction, for example as described further below, with regard to the method for correcting computerised radiographic tomography data.

Errors in image rotation can be corrected by measuring the inclination of the angles of the lines joining pairs of points: 15a, 15b; 15c, 15d; 15a, 15c; and 15b, 15d, for example as described further below, with regard to the method for correcting computerised radiographic tomography data.

Further, in the case where the registration object has an outer surface which is cylindrical or conical about the Z-axis, or has an inner surface which is cylindrical or conical about the Z-axis, the lines defining these surfaces in the projection can also be used to obtain dimensions and to correct the projection, in terms of rotation in the image plane, in terms of offset in the axial and cross-axis direction, and in terms of magnification, for example as described further below, with regard to the method for correcting computerised radiographic tomography data.

Figure 10:
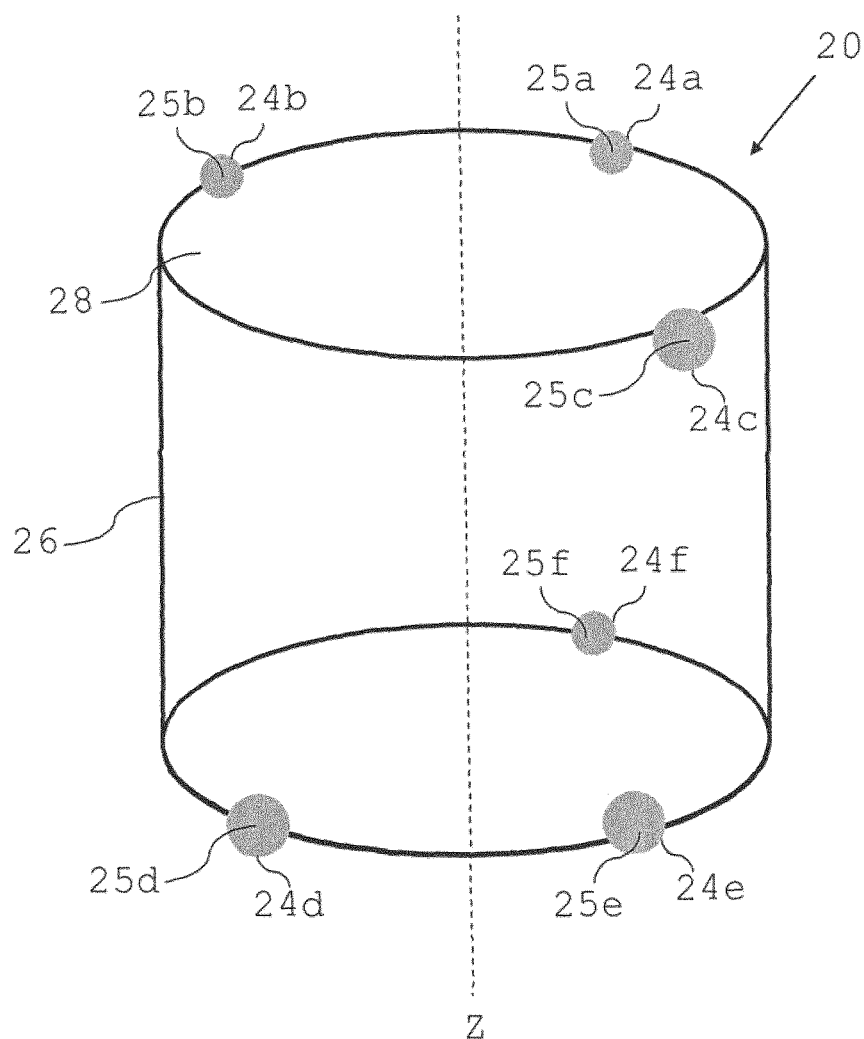
FIG. 10 shows a variant embodiment of a registration object.

FIG. 10 shows a further variant embodiment of the registration object.

FIG. 10 shows registration object 20 in perspective view. Registration object 20 has three relatively radiopaque elements 24a, 24b, 24c arranged on a first plane crossing the Z-axis. The radiopaque elements are supported by a support structure 28 which is relatively radiolucent, which defines an internal void 26, and which supports the radiopaque elements in predetermined positions on the first plane. Since there are three radiopaque elements, at least two radiopaque elements will be visible in each projection about the Z-axis, even if an object is contained within the void at a height crossing the first plane.

As the object rotates, the positions in a corresponding sequence of x-ray projections of each radiopaque elements 24a, 24b and 24c will change, as well as their sizes. Accordingly, two of the visible radiopaque elements, for example the two radiopaque elements outermost in projection from the Z-axis, or the two radiopaque elements which are judged to be most forward in the projection, can be used to define registration points to obtain dimensions and to correct the projection, in a similar way to registration points 15a and 15b. For example, the centroid of each visible radiopaque elements may be assigned as a registration point, and the outermost two registration points may be assigned as registration points 25a, 25b. For projections in which more than one radiopaque elements is visible, measurements relating to the third radiopaque elements may be discarded, or may be included in calculations to improve accuracy as defining a third registration point 25c.

For the occasional projection frame of a sequence acquired about the Z-axis in which two radiopaque elements partly or fully overlap, it may be decided to track the larger of the two radiopaque elements which overlap. Alternatively, if such tracking is not possible, it may be chosen to predict from previous frames the positions of the overlapping radiopaque elements, or to interpolate correction data from neighbouring frames. Reducing the diameter of the radiopaque elements can tend to reduce the incidence of overlap, while increasing the diameter of the radiopaque elements can tend to make the radiopaque elements more easy to identify in projections, and can improve the accuracy of the identification of the registration points. Preferably, the registration points are defined as centres, and more preferably centroids, of the radiopaque elements, which may be particularly straightforward to determine in automated image processing.

Additionally, registration object 20 has three further substantially radiopaque elements 24d, 24e, 24f arranged on a second plane, which crosses the z-axis preferably at a different location. The principles of determining registration points 25d, 25e, 25f from the centroids of radiopaque elements 24d, 24e and 24f is essentially similar to that for determining registration points 25a, 25b, 25c.

In the present embodiment, each plane of the first and second planes is perpendicular to the Z-axis and crosses at a different point. This may simplify automated image-processing to determine correction factors. However, using inclined planes is possible and may be preferred to allow a set of coplanar radiopaque elements also to provide information with regard to the along-axis as well as cross-axis direction. Slight inclination of the planes may also avoid occulusion of coplanar elements in sequences of projections about an axis.

In the present embodiment, the radiopaque elements on each plane of the first and second planes are of geometrically similar shape and substantially the same size. This also may simplify automated image-processing to determine correction factors. Each radiopaque element on a plane may have one or more axes of symmetry, and one or more axis of symmetry of each element on a given plane of the first and second planes may be aligned or oriented towards a given direction, for example aligned with or oriented toward the Z-axis. However, radiopaque elements of different sizes and/or shapes may in some circumstances be easier to track and distinguish. In such cases, even if the radiopaque elements on a plane themselves do not have spherical symmetry, or are not identical, they may share a common external diametric dimension, that is, at least one external dimension of each radiopaque element is the same as at least one external dimension of each of the other radiopaque elements on the same plane.

In the present embodiment, the radiopaque elements are spherical, and for reasons of radiopacity may be filled and thus also spheroidal. Finding the centre or centroid of the projection of a sphere in an image may be particularly straightforward using conventional image-processing techniques and edge erosion effects are less significant. Further, for such structures, the centroids may be assigned to lie on the first and second planes, respectively.

In the present embodiment, there are three radiopaque elements on each plane, but the number of radiopaque elements may be increased. The radiopaque elements on a given plane may be arranged with a common distance from the Z-axis, may be arranged at common angular intervals around the Z-axis and/or may be arranged with common spacings between closest-neighbouring radiopaque elements on a given plane. The preceding remarks may apply to the radiopaque elements on each plane, or may apply to the radiopaque elements on both planes with the common distances, common angular intervals and common spacings being the same or different between each plane. In a limiting case, providing a large number of relatively small radiopaque elements arranged at a common radius from the z-axis, equal angular intervals and relatively close spacing will tend to the configuration, described above in relation to registration object 10, of an interrupted circumferential bead.

In some cases, the radiopaque elements may have similar configurations as between the first and second planes, but the configuration of the second plane is rotated about the Z-axis with regard to the configuration of the first plane. Such a configuration can avoid spheres on both planes being occluded by another sphere of the same plane at the same time.

Relatively radiolucent support structure 28 also need have no special configuration, although a thin-walled cylinder of relatively radiolucent material or mesh may be convenient to adopt for ease of manufacture and low radiodensity. However, thicker-walled structures or rigid posts extending from a base plate and optionally to a top plate are also contemplated, especially where greater structural rigidity is required. In some configuration, a network of rods linking the radiopaque elements may act as a support structure, the radiopaque elements being analogous to nodes on the network. For example, the radiopaque elements on each plane could be linked to their closest neighbours by struts, and the radiopaque elements of each plane linked to counterpart radiopaque elements on the other plane by similar struts. Support structure 28 may have rotational symmetry about the Z-axis, for example being one-fold, two-fold, three-fold or perfectly symmetric about the Z-axis.

Another variant is possible in which radiopaque elements 24a to 24f are arranged on the support structure on one or more helices, rather than one or more planes, about the z-axis. In such a case, the support structure could be provided as one or more helical wire or band along which the radiopaque elements are arranged. Such a configuration may adopt equal helix-angular spacings between neighbouring radiopaque elements along a helix, and may provide each radiopaque element on the helix as having a geometrically similar shape and size.

Additionally, more than two planes of radiopaque elements, or one or more planes and helices of radiopaque elements, may be combined in the same registration object, without limitation.

In relation to the above, it must also be understood that a combination is possible between the features of registration object 20 and registration object 10, without limitation. For example, a set of coplanar or helical radiopaque elements of registration object 20 may be combined with one or more circumferential beads or grooves of registration object 10. The registration object 10 may function as a support structure 28 for a set of radiopaque elements 24a to 24f described in relation to registration object 20.

In the above, the radiopaque elements may have the same or different compositions, and for example may be made of lead. All such combinations and modifications herein disclosed may be useful to achieve particular combinations of ease of image processing An apparatus and method for correcting computerised radiographic tomography data, also being embodiments of the present invention, will now be described.

Figure 8A:
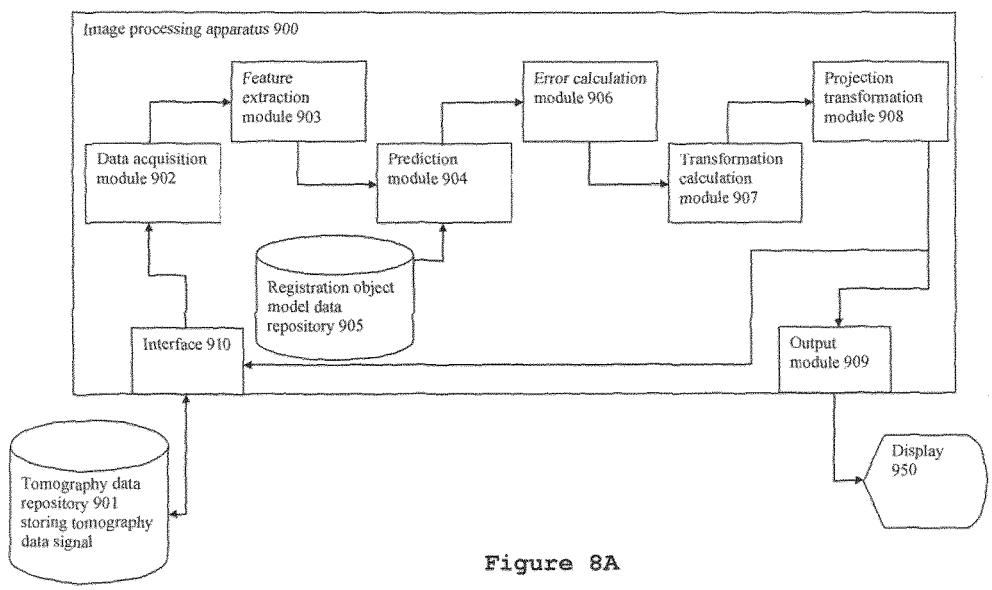
FIG. 8A shows a block diagram of an embodiment of an image processing apparatus for correcting CT data.
Figure 8B:
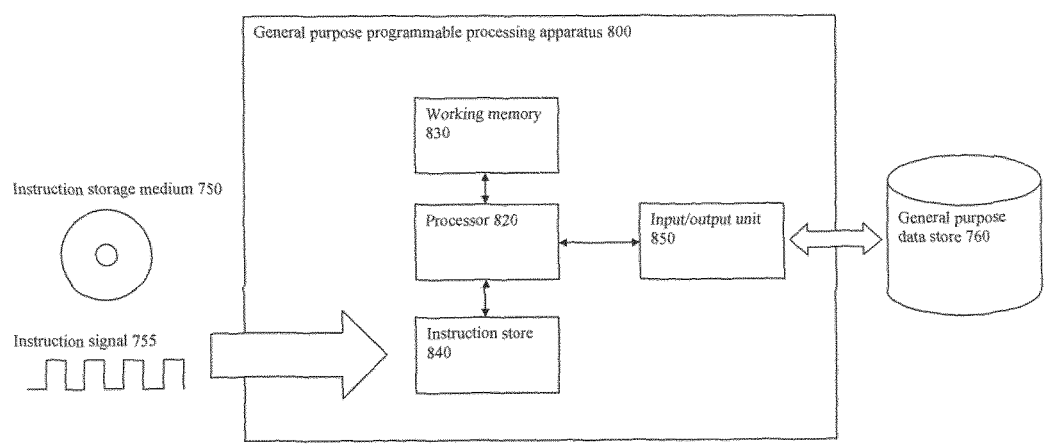
FIG. 8B shows a block diagram of a programmable processing apparatus suitable for programming to become operable to function as an image processing apparatus for correcting CT data.
Figure 9:
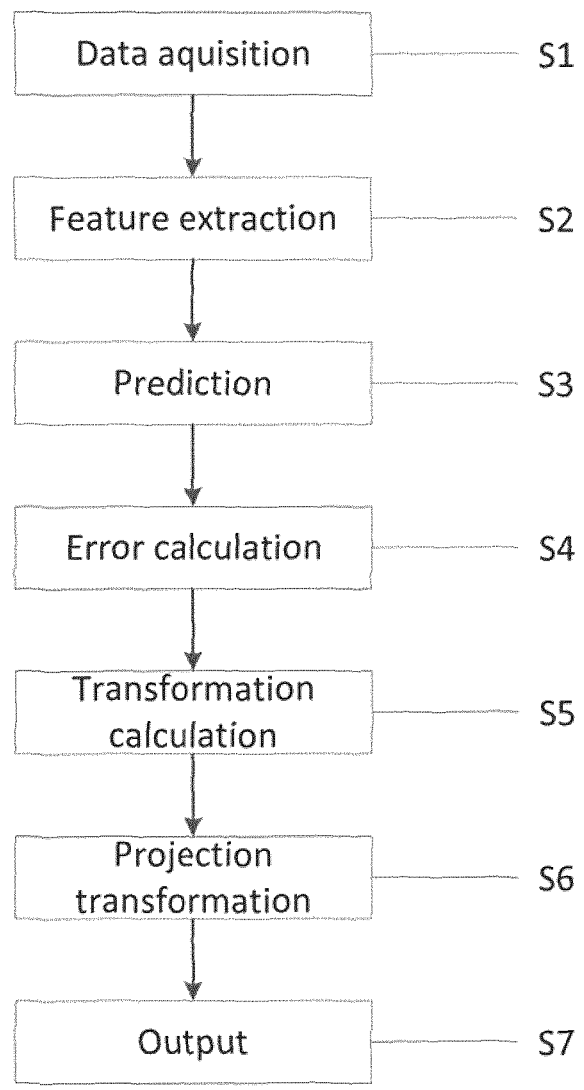
FIG. 9 shows a flow chart of a method of correcting CT data.

A general process for correcting computed tomography data can be understood in general with reference to the apparatus block diagram of FIGS. 8A and 8B and the flow diagram of FIG. 9. A specific embodiment will subsequently be described with reference to FIG. 7 and the previously-described exemplary reference object of FIG. 2. However, it is to be understood that the general approach may be applied in connection with any suitable reference object.

FIG. 8A shows image processing apparatus 900, as an exemplary apparatus by which the disclosed process can be performed. However, it must be understood that the apparatus of FIG. 8A is exemplary, and can be implemented using any appropriately-configured software modules, or by a suitably-programmed general purpose processing apparatus.

Image processing apparatus 900 has the following modular components: data acquisition module 902 for acquiring tomography data representing projections of a target object at a variety of angles about a predetermined axis; feature extraction module 903 for identifying registration features of a registration object in those projections; prediction module 904 for predicting the ideal location of those features under an ideal imaging process from a model of the registration object; registration object model data repository 905 (or alternatively a registration object model data signal) for storing the model of the object; error calculation module 906 for deriving errors in the acquired projections based on a comparison of positions of the identified registration features and the predicted ideal positions of the identified registration features; transformation calculation module 907 for calculating the required image transformations to negate the effect of the derived errors in the projections; projection transformation module 908 for applying the calculated transformations to the projections to obtain corrected projections; and output module 909 for generating rendered tomographic density maps from the corrected projections. It is connected to, or connectable to, tomography data repository 901 (or alternatively a tomography data signal). The module components can be implemented as software modules running on a single virtual processor, physical processor, or cluster of processors, or as discrete and task-dedicated processors.

An example of a general purpose programmable processing apparatus in which the image processing apparatus 900 may be implemented is shown in FIG. 8B. The general purpose programmable processing apparatus 800 shown comprises working memory 830 coupled to processor 820, which operates according to the instructions provided by instruction store 840.

The instruction store 840 is a data storage device which may comprise a non-volatile memory, for example in the form of a ROM, a magnetic computer storage device (e.g. a hard disk) or an optical disc, which is pre-loaded with the computer-readable instructions. Alternatively, the instruction store 840 may comprise a volatile memory (e.g. DRAM or SRAM), and the computer-readable instructions can be input thereto from a computer program product, such as a computer-readable storage medium 750 (e.g. an optical disc such as a CD-ROM, DVD-ROM etc.) or a computer-readable signal 755 carrying the computer-readable instructions.

Processor 820 is also connected to input/output unit 850, which provides an interface to an external general purpose data store 760. The general-purpose data store 760 can also, in some embodiments, provide the functions of the registration object model data repository 905, instruction store 840 and/or tomography data repository 901.

The working memory 830 functions to temporarily store data to support the processing operations executed in accordance with the processing logic stored in the instruction store 840. As shown in FIG. 8B, the I/O unit 850 is arranged to communicate with the processor 820 so as to render the apparatus capable of processing received signals and communicating its processing results.

In the present embodiment, the combination of the processor 820, working memory 830 and the instruction store 840 (when appropriately programmed by techniques familiar to those skilled in the art) together constitute the data acquisition module 902, feature extraction module 903, prediction module 904, registration object model data repository 905, error calculation module 906, transformation calculation module 907, and projection transformation module 908 of the image processing apparatus 900. This combination performs the operations of the image processing apparatus that are described herein.

FIG. 9 shows a flow chart of the processing operations performed by the image processing apparatus in one embodiment.

The flow diagram of FIG. 9 has a first process S1 of acquiring data representing a sequence of radiographic projections about a tomographic axis of a registration object at least partially enclosing a target object. This first process can be performed either by performing a tomographic imaging sequence with a CT system or by loading data from a previously-performed imaging sequence from a data repository. In the exemplary apparatus 900 of FIG. 8A, the data is stored in repository 901 and acquired through interface 910.

Once the data is acquired, a second process S2 can be performed. The second process is the processing of each projection of the set of projections to identify and determine the positions of one or more registration points of known geometry in the projection. This can be performed by, for example, shape-matching in each image with feature extraction module 903. Additionally or alternatively, the positions of edges of the registration object can be identified using edge detection.

In some cases, a candidate point for each registration point is easily determined. In other cases, more than one candidate point can be determined and associated with each registration point. Probabilistic or analytical techniques can then be used to compare candidate points between images to uniquely identify one candidate point with each required registration point. In some projections, no candidate point may be identified; these projections can be excluded from the set of projections from which correction data is to be determined, but can be subsequently included in the set of projections to which the correction data is to be applied, as will be described.

The positions are determined in the horizontal (cross-axis) and vertical (along-axis) directions, such that at least two points different in vertical position are identified and at least two points different in horizontal position are identified.

As a next process S3, known data about the registration object stored in registration object model data repository 905 is used by prediction module 904 to predict the ideal positions of the registration points in each projection. The known data can be, for example, a set of relative positions and spacings of registration features at defined projection angles, or a mathematical model of how the registration features are expected to behave under ideal imaging conditions as a function of angle of projection. The known data about the registration object can also be a signal representing the positions and relative spacings of the registration features giving rise to the registration points, and functions defining whether and how these positions and spacings vary according to angle about a predetermined axis of the object.

The registration object model data therefore allows error calculation module 906 to predict where the registration points of the registration object should appear in each of the acquired projections, under ideal and error-free imaging conditions. The identified positions of the registration points can also be used to inform the determination of the predicted positions of the registration points, for example in a case where parameters of the model, such as amplitude of sinusoidal motion or gradient and offset of linear motion, are undefined in the model and thus determined by fitting the identified positions of the registration points with angle to a function defined by the model. The parameters thus derived can then be incorporated in the model to determine the predicted positions.

Once the required registration points are identified and the predicted positions are generated, the positions of the identified registration points are compared with the predicted positions of the respective registration points as a next process S4 by error calculation module 906.

At this point also, information as to the angle from which the projection was acquired can obtained from a record in the acquired data or can be inferred from the behaviour of the positions of the registration points as between successive projections in the sequence of projections, again with reference to the model.

The identified positions of the registration points in the projections can thus be compared by the error calculation module 906 with the predicted positions and the deviations from the predicted positions of the registration features can be calculated as error data. For example, the predicted positions of the registration points in each projection can be determined based on the known data about the registration object. The predicted positions of the registration points can then be subtracted from the determined positions of the registration points for each projection to provide a set of residual errors for each projection.

Once the error data for each projection is known, correction data for each projection of the sequence of projections can be calculated in a next process S5 by the transformation calculation module 907, in the form of the image transformations, such as scaling, rotation and/or offset, which are needed to transform the identified positions of the registration features to be closer to the predicted positions of the registration features, in order to obtain a corrected projection. Such data can be represented, for example, as a transformation matrix for application to the projection data represented in matrix form.

Optionally, synthetic correction data can also be determined by the transformation calculation module for any projections forming part of the acquired sequence but for which registration points could not be determined. For example, a confidence value can be assigned to each registration point based on the ease of identification of the registration point in a given image. If the registration point cannot be detected with sufficient confidence, synthetic correction data can be used in place of correction data derived from the registration point. Synthetic data can also be used in the event that a point is detected at an unexpected location, which would suggest an inaccurate detection, or is not detected at all. Such synthetic correction data can be obtained by interpolation between determined correction data for neighbouring or proximate projections in the sequence.

The correction data thus obtained can then be applied in a next process S6 by the projection transformation module 908, appropriately, to each projection of the acquired sequence of projections to obtain corrected projection data, as a next process. For example, matrix data representing each projection can be transformed by application of the matrix representing the correction data.

In the apparatus of FIG. 8, all processes S11 to S6 processes are carried out by a processor, and corrected projection data are returned to the repository 901 to supplement or replace the acquired data. However, FIG. 8 also provides an optional output module 909, which in an optional output step S7 reconstructs the corrected projection data into a tomographic volume map of the target object in the form of a 3D voxel set, and optionally displays it on a display (950).

It is important to note that the processes of the described process of FIG. 9 have been described as sequential operations on a set of projections, the whole set being processed at each process. While in many situations such a batch approach is preferred, for some classes of projection data it may be preferred to process each projection of the acquired data individually to obtain a corrected projection before the next projection in the sequence is processed. Such sequential processing requires fewer resources, and with sufficient processing power can provide corrected projections in real time during CT sequence acquisition, but cannot take advantage of comparisons between all projections in the set of projections to associate candidate points with registration points or to determine best fit curves of registration points to the known data about the registration object. In a hybrid approach, the projections are processed sequentially, but information obtained from previous projections in the sequence is used to improve the quality of corrections applied to subsequent images.

The mentioned techniques can be applied to any of the variant embodiments of the registration object described above, with suitable modification. In the most general form of the technique, once the positions of registration points in each projection are identified, the image can be transformed in terms of horizontal and vertical scaling and in terms of image rotation such that the registration points map onto the locations at which they are predicted to exist from information relating to the physical structure of the registration object. Interpolation can be generally used to determine correction data for projections in which the registration points are not identifiable, whether due to the design of the registration object, or due to other imaging factors. One skilled in the art will be able to extend and adapt this teaching, as appropriate, to suit his individual situation.

As a particular embodiment of the image correction process, reference will now be made to FIG. 9 and to an exemplary image correction process which is performed by an image processing apparatus of an embodiment in connection with the exemplary registration object of FIG. 2. However, its use is not limited thereto, and indeed the same technique may be used, in suitably adapted form, with any of the variant embodiments described, or with other embodiments of the present invention which are not described, but which fall within the broadest scope of the registration object herein disclosed.

Firstly, as an example of the process S1, a set of computerised radiographic tomography data of a target object T is acquired into the image processing apparatus 900 by the data acquisition module 902. Such data is assumed in this example to originate from the use of the registration object of FIG. 2, adopting the geometry of FIG. 1. In such a situation, the registration object of FIG. 2 is placed such that the axis Z is coincident with, or at least parallel to, the axis A and such that target object T lies within void 16. The set of radiographic projections of the target object is acquired at a series of angles about axis A. Such an imaging process results in a signal or stored data representing the set of radiographic projections, and may be stored in tomographic data repository 901, or transmitted as a data stream or signal to the image processing apparatus 900 over a suitable datalink or network. The image processing apparatus can form part of the CT acquisition system from which the projections are acquired, or can be a distinct apparatus.

Next, as an example of the process S2, in the example of FIG. 7, the positions of the four tips of the four V-shaped grooves can be calculated using the feature extraction module 903, for example by using edge detection to fit best-fit sloping lines to the inner surfaces of the grooves and finding the points of intersection of these lines. The registration points 15a, 15b, 15c and 15d are thus identified with each of these tips.

The inner and outer walls of the registration object on each side of the image ($O_L$, $I_L$, $O_R$, $I_R$) can be identified by fitting a best-fit vertical straight line to points found by edge detection.

Next, as an example of the process S3, model data about the registration object is used to predict the ideal positions of the reference points in each projection. In the model adopted for the purposes of the present example, the positions of the registration points and the walls are assumed to be constant in the projection under ideal imaging conditions. This information about the model is stored internally to the image processing apparatus 900 by means of registration object model data repository 905. However, such information could also be externally supplied either together with or separate from the acquired tomography data.

Next, as an example of the process S4, known data about the registration object is compared with the identified registration points by the error calculation module 906 to provide error data.

The horizontal positions $x_1$, $x_2$ of the points $p_1$, $p_2$ where the mid-line of the outer and/or inner vertical walls on the left and on the right side of the image ($C_L$, $C_R$) crosses the horizontal image centre line ($Z_H$) can be calculated. Movement of the average of these positions from image to image gives the relative horizontal shift of the target object.

Alternatively, the horizontal position of the point where the mid-line ($R_V$) between the two vertical lines ($R_L$, $R_R$) connecting the two registration points associated with the respective left and right sides of the object crosses the horizontal image centre line ($Z_H$) can be calculated. Movement of this position from image to image also can give the relative horizontal shift of the target object.

The vertical positions $y_1$, $y_2$ of the points $p_3$ and $p_4$ where the two horizontal lines ($R_T$, $R_B$) connecting the tips of the two Vs associated with each groove 13, 14 crosses the vertical image centre line ($Z_V$) can be calculated. Movement of the average of these positions from image to image gives the relative vertical shift of the target object.

Alternatively, the vertical position of the point where the mid-line ($R_H$) between the two horizontal lines ($R_T$, $R_B$) connecting the tips of the two Vs associated with each groove 13, 14 crosses the horizontal image centre line ($Z_H$) can be calculated. Movement of this position from image to image also can give the relative vertical shift of the target object.

Changes in the distance between the two points $p_1$ and $p_2$ where the two vertical mid-lines ($C_L$, $C_R$)) between the outer and inner walls on the left and the right of the registration object cross the horizontal image centre line ($Z_H$) measured perpendicular to the mid-line (not shown) between these lines gives the change in horizontal magnification of the target object $M_H$.

Alternatively, changes in the distance between the two points where the two vertical lines ($R_L$, $R_R$) connecting the tips of the two Vs associated with each side of the registration object cross the horizontal image centre line ($Z_H$) measured perpendicular to the mid-line between these lines ($R_V$) gives the change in horizontal magnification of the target object.

Changes in the distance between the two points where the two horizontal lines ($R_T$, $R_B$) connecting the tips of the two Vs associated with each groove crosses the vertical image centre line ($Z_V$) measured perpendicular to the mid-line between these lines ($R_H$) gives the change in vertical magnification of the target object $M_V$.

An average magnification factor change M can be calculated as the average of the change in horizontal magnification $M_H$ and the change in vertical magnification $M_V$. In many imaging scenarios, the horizontal magnification can be assumed to be approximately equal to the vertical magnification. Accordingly, calculating an average magnification factor change can provide a better estimate of the magnification factor correction to be applied to the image.

The average of the angle $\alpha_1$ anti-clockwise from horizontal of the lines ($R_T$, $R_B$) connecting the two Vs associated with each groove and the angle $\alpha_2$ anti-clockwise from the vertical of the lines ($R_L$, $R_R$) connecting the tips of the two Vs associated with each side of the registration object gives a rotation angle of the image.

Accordingly, the horizontal and vertical movements, the magnification changes and the rotations can all be calculated.

From these error values, as an example of process S5, a set of transformations are calculated by transformation calculation module 907 to compensate for the errors which, when applied to the projections, will result in the projections being corrected to keep all movements and angles to zero and all scale change factors to one, by means of suitable image transformation operations such as shifting, scaling, and rotating.

For example, an average rotation $\alpha$, being the average of $\alpha_1$ and $\alpha_2$, can be calculated and the projection rotated clockwise about its centre point by this angle. Mathematically, this can be represented as $x' = x \cos \alpha - y \sin \alpha$; $y' = y \cos \alpha + x \sin \alpha$; where x' and y' are the pixel co-ordinates of the transformed image and x and y are the pixel co-ordinates of the untransformed image, and $x' = x = 0$ and $y' = y = 0$ in the centre of the image Further, an average horizontal shift $\delta x$ can be calculated as the average of $x_1$ and $x_2$, and the image shifted left (negative X direction) by this distance. Mathematically, this can be represented as $x' = x + \delta x$.

Similarly, an average vertical shift $\delta y$ can be calculated as the average of $y_1$ and $y_2$, and the image shifted downwards (negative Y direction) by this distance. Mathematically, this can be represented as $y' = y + \delta y$.

Finally, the image can be scaled by 1/M about its centre. Mathematically, this can be represented as $x' = x/M$; $y' = y/M$.

The correction factors can be smoothed between projections for example using a moving average, to avoid errors due to noise, provided that the number of projections used is sufficiently high.

Based on these transformations, as an example of process S6, the transformations calculated can be applied by projection transformation module 908 to each projection by straightforward pixel-wise transformation operations.

Finally, as an example of process S7, the transformed projections are output by output module 909, either to data repository 901 to supplement or supplant the original tomography data or as a further signal or datastream. Additionally, in the output step, information as to actual measured relative positions of the registration points, length of the object and the actual inner and outer diameters, or the average thickness of the wall, can provide an absolute scale factor, so that the acquired images can be related to real-world measurements in a dimensionally accurate manner.

In a modification of the above approach, rather than fitting the identified horizontal reference positions (whether points or lines) to fixed respective horizontal positions in the image before reconstruction, the reference positions can be fitted to a sinusoid. These sinusoidally-varing positions are predicted in step S3 and can then be subtracted in process S4 from the identified horizontal positions, and then the residual differences can be used as the correction data.

In such a modification, the target object and registration object will perform a sinusoidal motion in the sequence of acquired projections, and the volume map derived from those projections will have as a central axis the axis of relative rotation of the source, rather then the axis of symmetry of the registration object. This can, in some cases, provide a much sharper reconstruction, especially when an axis of cylindrical symmetry of the reference object is not substantially coincident with the axis of relative rotation of the source-detector system, and especially in the case in which the magnification of the object appears to vary substantially over a complete CT cycle.

Additionally, or alternatively, the vertical reference positions can also be fitted to sinusoids to account for the generally smaller in amplitude, but nonetheless present, sinusoidal variation in magnification in the same situation, as the object moves closer to and then away from the detector over a complete CT imaging cycle. In such a case, points above the imaging centreline (i.e. $Z_H$ in FIG. 7) move in a sinusoidal movement of substantially identical amplitude and period as, but out of phase to, equivalent points below the imaging centreline.

In another modification of the above, rather than a registration object in which the registration points are fixed in each projection about the predetermined axis, a registration object in which the registration points have positions in projections according to a continuous function of the angle of the projection about the predetermined axis may be provided. For example, the features could be formed helically about the predetermined axis. In such a case, information about the function is needed in the correction method. For example, in the case of helical features, such as a groove or bead formed as a screw thread, the positions of the registration points in the vertical (axial) direction will vary linearly with rotation angle in a well-defined way. Appropriately, the vertical reference positions should be fitted to a best-fit linear function, the best-fit linear function can then be subtracted from the determined vertical positions, and then the residual differences can be used as the correction data.

Similarly, when using, for example, as reference points features of the radiopaque elements 24a to 24f of the registration object 20 shown in FIG. 10, the method may need adaption to the particular geometry selected. With reference to FIG. 10 and by comparison to FIGS. 2 and 7, radiopaque elements 24a, 24b and 24c will orbit about the axis of rotation and thus in ideal projection circumstances will in projection describe sinusoidal motion with rotation about the Z-axis along a first line crossing the vertical axis. Similarly, radiopaque elements 24d, 24e and 24f will describe sinusoidal motion along a second line crossing the vertical axis at a different point. The line joining the centroids of radiopaque elements 24a, 24b and 24c and the line joining the centroids of radiopaque elements 24d, 24e and 24f may correspond to the lines $R_T$, $R_B$ shown in FIG. 7, while the known configuration of the radiopaque elements on each plane can be used to define a circle on each plane whose length along the equivalent lines to $R_T$, $R_B$ can be used to define equivalent lines to $O_L$, $I_L$, $O_R$, $I_R$. In each case, comparison of the expected positions of the reference points with the determined positions of the reference points in each acquired projection of a sequence of projections may permit correction data to be acquired for that projection.

In some projections, the features may not be visible, or may not be detected with confidence, for example due to occlusion with radiodense material or manufacturing imperfections. Even though providing the reference object to surround at least part of the sample, and/or using reference features which lie on a cylindrical surface surrounding at least part of the sample will tend to minimise this possibility, in some scenarios reliable detection of the features in each projection may not be guaranteed. In such scenarios, interpolation between projections in which the features are visible can be used to correct those projections in which the features are not. For example, those projections in which the features are visible can be detected, and then the correction data can be extracted from those projections alone. The correction data can then be applied, with any suitable interpolation, to the projections in which the features are not visible, according to their relationship in the sequence to the projections in which the features are visible. For example, linear, polynomial or sinusoidal interpolation can be used, depending on the level of accuracy required.

It is expected that one skilled in the art will be able to modify and adapt the above disclosure to suit his own circumstances and requirements within the scope of the present invention, while retaining some or all technical effects of the same, either disclosed or derivable from the above, in the light of his common general knowledge of the art. All such equivalents, modifications or adaptions fall within the scope of the invention here claimed.

The invention claimed is:

1. A method of correcting computed radiographic tomography data, comprising the process of:
   acquiring data representing a set of radiographic projections of a target object and a registration object including at least part of the target object within the void of the registration object at a series of angles about the predetermined axis;
   determining in each projection the positions of registration points defined by the registration object;
   comparing stored information about the registration object with the determined positions of the registration points to obtain projection correction information for each projection;
   applying the projection correction information to each projection to provide a set of corrected radiographic projections.

2. The method of claim 1, wherein the process of comparing includes processes of:
   predicting positions of the registration points in each projection based on stored information about the registration object,
   comparing predicted positions of the registration points in each projection with the determined positions of the registration points in each projection, and
   calculating projection correction information based on the differences between the predicted and determined positions of the registration points in each projection.

3. The method of claim 2, wherein at least two of the registration points are predicted to appear at positions which vary sinusoidally in the projections with respect to projection angle.

4. The method of claim 2, wherein at least two of the registration points are predicted to appear at positions which vary linearly in the projections with respect to angle.

5. The method of claim 1,
   wherein the set of radiographic projections are selected from a larger set of radiographic projections obtained from the same tomographic acquisition sequence.

6. The method of claim 1,
wherein the process of acquiring the data representing a set of radiographic projections includes the process of performing a tomographic acquisition sequence on the at least part of the target object enclosed by the registration object.

7. The method of claim 1,
data representing a set of radiographic projections includes the process of loading data acquired during a tomographic acquisition sequence on the at least part of the target object enclosed by the registration object from a data repository.

8. The method of claim 1,
further comprising the process of reconstructing a tomographic volume map from the set of corrected radiographic projections.

9. The method of claim 1, wherein the positions of at least a pair of identifiable registration points which are spaced apart in a direction parallel to the predetermined axis by a first distance and a pair of identifiable registration points which are spaced apart in a direction perpendicular to the predetermined axis by a second distance are determined.

10. The method of claim 1, wherein the projection correction information comprises at least one of relative axial shift, relative cross-axis shift, relative axial magnification, relative cross-axis magnification, relative average magnification and absolute scale factor.

11. The method of claim 1, wherein the process of determining the position of the registration points employs one of edge detection or shape detection.

12. The method of claim 1, wherein the projection correction information relates to one or more of translation, rotation and magnification of the image.

13. The method of claim 1, wherein the method further comprises a process of reconstructing the corrected projections into a tomographic volume density map.

14. The method of claim 1, wherein the steps of acquiring, determining, comparing and applying are performed in sequence to each radiographic projection in turn.

15. The method of claim 1, wherein each of the steps of acquiring, determining, comparing and applying is performed in turn to the whole set of radiographic projections.

16. The method of claim 1, wherein the projection correction information is smoothed between projections.

17. An apparatus for correcting computed radiography tomography data, comprising:
a data acquisition module for acquiring data representing a set of radiographic projections of a target object and a registration object including at least part of the target object within the void of the registration object at a series of angles about the predetermined axis;
a feature extraction module for determining in each projection the positions of registration points; a prediction module for predicting positions of the registration points in each projection;
an error calculation module for comparing stored information about the registration object with the determined positions of the registration points to obtain error information for each projection;
a transformation calculation module for determining transformations based on the error information; and
a projection transformation module for applying the transformation to each projection to provide a set of corrected radiographic projections.

18. A storage medium storing computer program instructions to program a programmable processing apparatus to become operable to perform the method according to claim 1.

19. A signal carrying computer program instructions to program a programmable processing apparatus to become operable to perform the method according to claim 1.

20. The apparatus according to claim 17, wherein,
the registration object has a body portion defining a void for including at least part of a target object, and
the registration object comprises one or more relatively radiopaque or relatively radiolucent features,
said feature or features providing, for substantially all radiographic projections of the registration object with respect to angle about a predetermined axis, a pair of identifiable registration points which are spaced apart in a direction parallel to the predetermined axis by a first distance, and whose positions in that direction are each either a constant or a function only of the angle of the projection about the predetermined axis and
said feature or features providing, for substantially all radiographic projections of the registration object with respect to angle about a predetermined axis, a pair of identifiable registration points which are spaced apart in a direction perpendicular to the predetermined axis by a second distance whose positions in that direction are each either a constant or a function only of the angle of the projection about the predetermined axis.

21. The apparatus according to claim 20, wherein the feature or features provide the registration points for all radiographic projections.

22. The apparatus of claim 20, wherein the feature or features have substantially the same shape or shapes in each radiographic projection of the registration object about a predetermined axis.

23. The apparatus of claim 20, wherein said feature or features are arranged to lie on and extend circumferentially about a surface of rotation about the predetermined axis.

24. The of apparatus of claim 20, wherein said feature or features are arranged to lie on and extend circumferentially about a cone having the predetermined axis.

25. The apparatus of claim 20, wherein said feature or features are arranged to lie on, and extend circumferentially about, a cylinder having the predetermined axis.

26. The apparatus of claim 20, wherein the position of at least one of the registration points is defined by an invertible function of the angle of the projection about the predetermined axis.

27. The of apparatus of claim 20, wherein the position of at least one of the registration points is defined by a linear function of the angle of the projection about the predetermined axis.

28. The apparatus of claim 20, wherein said feature or features comprise one or more grooves.

29. The apparatus of claim 20, wherein said feature or features comprises one or more radiopaque beads.

30. The apparatus of claim 20, wherein said feature or features comprises one or more radiopaque elements arranged at positions having different distances along the predetermined axis and having different distances across the predetermined axis.

31. The apparatus of claim 30, wherein said feature or features comprises at least three radiopaque elements arranged at different positions on a first plane which crosses the predetermined axis at a first position.

32. The apparatus of claim 31, wherein said feature or features further comprises an additional at least three radiopaque elements having arranged at different positions on a second plane which crosses the predetermined axis at a second position different from the first position.

33. The apparatus of claim 32, wherein said first plane and said second plane are parallel.

34. The apparatus of claim 33, wherein said first plane and said second plane are perpendicular to the predetermined axis.

35. The apparatus according to claim 31, wherein for at least one plane selected from the first and second planes, each element of the radiopaque elements arranged on that plane is equally spaced from a respective closest neighbouring element of the elements arranged on that plane.

36. The apparatus according to claim 31, wherein for at least one plane selected from the first and second planes, each element of the radiopaque elements arranged on that plane is arranged to have equal angles from a respective closest neighbouring radiopaque element of the radiopaque elements on that plane with respect to the predetermined axis.

37. The apparatus according to claim 31, wherein for at least one plane selected from the first and second planes, each element of the radiopaque elements arranged on that plane has a geometrically similar shapes to the other elements arranged on that plane.

38. The apparatus according to claim 37, wherein the said radiopaque elements arranged on one or both of the first plane or the second plane are substantially spherical.

39. The apparatus according to claim 31, wherein the said radiopaque elements arranged on one or both of the first plane or the second plane have at least one common external diametric dimension.

40. The apparatus of claim 20, wherein said feature or features comprises one or more helical circumferential features.

41. The apparatus of claim 20, wherein said feature or features comprises one or more annular circumferential features.

42. The apparatus of claim 20, wherein the void extends to at least one surface of the body portion.

43. The apparatus of claim 20, wherein the body portion comprises first and second partial portions which are releasably engageable to enclose the at least part of the target object.

44. The apparatus of claim 20, wherein the void is defined by a surface of rotation about the predetermined axis.

45. The apparatus of claim 20, wherein the body portion is one of a homogenous structure, a mesh structure, and a scaffold structure.

46. The apparatus of claim 20, wherein the body portion is a cylindrical sleeve having a cylindrical bore.

47. The apparatus of claim 20, wherein the body portion comprises a mount point for mounting the at least part of the target object in a desired position and orientation.

48. The apparatus of claim 20, defining a base surface in a plane perpendicular to the predetermined axis and on which the object is able to rest stably.

49. The apparatus of claim 48, wherein the void extends to the base surface.

* * * * *